US009383260B1

(12) United States Patent
Yoo et al.

(10) Patent No.: US 9,383,260 B1
(45) Date of Patent: *Jul. 5, 2016

(54) LASER ABLATION ANALYSIS SYSTEM

(75) Inventors: Jong Huyn Yoo, Milpitas, CA (US);
Randolph S. Tribe, San Jose, CA (US);
Chunyi Liu, Union City, CA (US)

(73) Assignee: Applied Spectra, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/492,923

(22) Filed: Jun. 10, 2012

Related U.S. Application Data

(63) Continuation-in-part of application No. 12/435,970, filed on May 5, 2009, now Pat. No. 8,199,321, which is a continuation-in-part of application No. 12/939,095, filed on Nov. 3, 2010, now Pat. No. 9,061,369.

(60) Provisional application No. 61/126,633, filed on May 5, 2008, provisional application No. 61/257,802, filed on Nov. 3, 2009.

(51) Int. Cl.
*G01J 3/30* (2006.01)
*G01J 3/443* (2006.01)

(52) U.S. Cl.
CPC ........................................ *G01J 3/443* (2013.01)

(58) Field of Classification Search
CPC .............. G01N 21/63; G01J 3/30; G01J 4/00; G06F 19/00
USPC ......... 356/318; 219/121.83; 250/309; 703/22
See application file for complete search history.

(56) References Cited

U.S. PATENT DOCUMENTS

| | | | | |
|---|---|---|---|---|
| 4,668,860 A * | 5/1987 | Anthon | | 250/225 |
| 6,771,368 B1 * | 8/2004 | Chadwick | | 356/318 |
| 7,663,749 B2 * | 2/2010 | Levesque et al. | | 356/318 |
| 2003/0193023 A1 * | 10/2003 | Marsh | | 250/309 |
| 2006/0036425 A1 * | 2/2006 | Le Cocq et al. | | 703/22 |
| 2006/0180581 A1 * | 8/2006 | Swaringen et al. | | 219/121.83 |
| 2007/0046934 A1 * | 3/2007 | Roy | | 356/318 |
| 2008/0243412 A1 * | 10/2008 | Horie et al. | | 702/82 |
| 2009/0290151 A1 * | 11/2009 | Agrawal et al. | | 356/318 |

* cited by examiner

*Primary Examiner* — Tarifur Chowdhury
*Assistant Examiner* — Jamil Ahmed
(74) *Attorney, Agent, or Firm* — Daniel L. Flamm; Microtechnology Law & Analysis

(57) ABSTRACT

Systems, methods, compositions, and apparatus for laser induced ablation spectroscopy are disclosed. A sample site position sensor, stage position motors operable to move the stage in three independent spatial coordinate directions, and a stage position control circuit can move an analysis sample site to selected coordinate positions for laser ablation. Light emitted from a plasma plume produced with laser ablation can be gathered into a lightguide fiber bundle that is subdivided into branches. One branch can convey a first portion of the light to a broadband spectrometer operable to analyze a relatively wide spectral segment, and a different branch can convey a second portion of the light to a high dispersion spectrometer operable to measure minor concentrations and/or trace elements. Emissions from a plasma plume can be simultaneously analyzed in various ways using a plurality of spectrometers having distinct and/or complementary capabilities.

25 Claims, 12 Drawing Sheets

LASER ABLATION ANALYSIS SYSTEM

CROSS-REFERENCES TO RELATED APPLICATIONS

This present application is a continuation-in-part of co-pending application Ser. No. 12/435,970 filed May 5, 2009 which claims the benefit of U.S. Provisional Application No. 61/126,633 filed May 5, 2008 filed both of which are hereby incorporated by reference for all purposes.

FIELD OF THE INVENTION

The present disclosure relates generally to the art of chemical analysis, and more particularly relates to improved apparatus and methods for monitoring the composition of a substrate using spectroscopies based on laser induced ablation.

BACKGROUND

Restriction of hazardous substances by statutes such as the Directive on the Restriction of the Use of Certain Hazardous Substances in Electrical and Electronic Equipment 2002/95/EC (commonly referred to as the Restriction of Hazardous Substances Directive or RoHS) was adopted in February 2003 by the European Union. The state of California has passed a similar law. The directive restricts the use of six hazardous materials in the manufacture of various types of electronic and electrical equipment. The six hazardous materials include Lead, Mercury, Cadmium, Hexavalent chromium (Cr-VI or Cr6+), Polybrominated biphenyls (PBB), and Polybrominated diphenyl ether (PBDE).

Industry seeks efficient and economical measures to comply with RoHS. Dissolution in acid is commonly used to test and measure compositional qualities of sample material. This method has inherent disadvantages. Laser induced breakdown optical emission spectroscopy (LIBS) as well as other laser spectrometry methods are potentially efficient and economical techniques to determining and/or verify the composition of products and other materials.

The LIBS type of spectrometry has been an unreliable and inexact measurement system since there is a large variation in the recorded data. A factor is the inconsistent plasma plume created by the pulse laser. Former LIBS type analyses have been unsuccessful in matching known standards achieved with other analysis methods.

SUMMARY

In a first aspect of the present disclosure, a laser ablation spectroscopy apparatus is provided. A pulsed laser is focused on a sample site to generate a plasma plume during a laser ablation process. The plasma plume can be detected with an optical spectrometer having an intensified charge coupled device. A sample of material is coupled to a stage movable in independent x, y and z directions using an array of x-y-z motors. A change in the height of the sample is detected using a sensor. Preferably, the sensor is a triangulation sensor. The apparatus includes a system computer for synchronizing the movement of the stage in the x, y and z direction during the laser ablation process. The height of the sample site can be automatically adjusted following each laser ablation. In one embodiment, the system computer includes a controller, application software and a graphical user interface (GUI).

In another aspect of the present disclosure, a method of laser ablation spectroscopy is provided. The method includes a protocol of generating one or more laser ablations to a sample site. The spectral data of the total number of laser ablations for the sites are averaged together. In some embodiments, the total number of laser ablations for a sample site equals three laser ablations. The protocol includes laser ablating additional sample sites and averaging the spectral data of the total number of sample sites. In some embodiments, there can be more than 20 sample sites.

Other features will become apparent from consideration of the following description taken in conjunction with the accompanying drawings.

BRIEF DESCRIPTION OF DRAWINGS

Various embodiments are illustrated in an exemplary manner by the accompanying drawings. The drawings and accompanying description should be understood to explain principles of the embodiments rather than be limiting. Other embodiments will become apparent from the description and the drawings.

DETAILED DESCRIPTION

Figure 1:
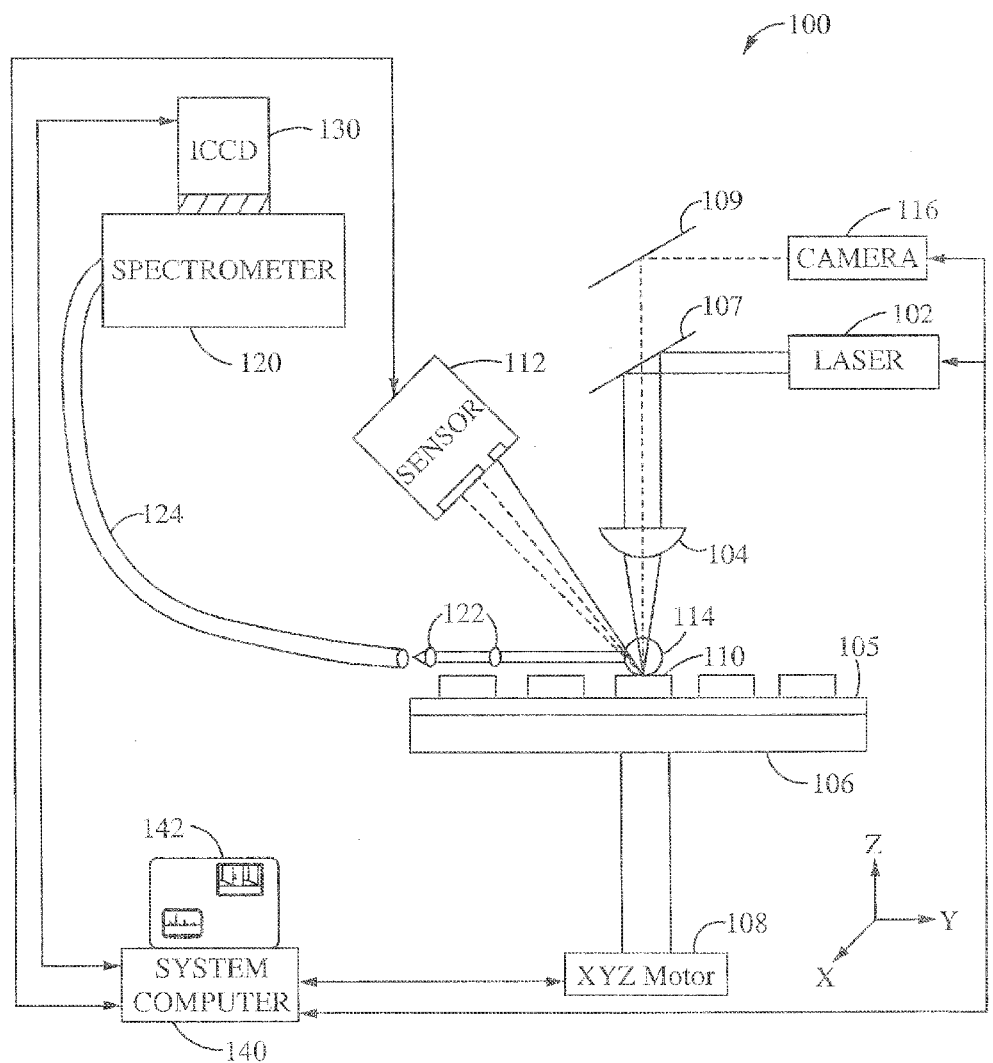
FIG. 1 a simplified diagram of a laser ablation apparatus embodiment.

Systems, methods, compositions, and apparatus for providing novel laser induced ablation spectroscopy are disclosed. In various embodiments, an apparatus comprises a sample site position sensor, stage position motors operable to move the stage in three independent spatial coordinate directions, and a stage position control circuit to move an analysis sample site to selected coordinate positions for laser ablation, with no human interaction. The ablation of material from an analysis sample site can displace its position from a point where the laser beam has a predetermined spot size. The embodiments can have a laser position sensor to detect a change in the position of the sample site and generate a displacement signal operable for the stage position control circuit to return the sample site to an original position using the stage motors.

In various embodiments, collection optics can gather light from a plasma plume produced with a laser ablation. The collection optics can couple the gathered light into a first end of a lightguide through which the light can be transmitted to a spectrometer. The lightguide can be a single fiber optic bundle including a plurality of optical fibers held generally parallel to one another in a geometric arrangement. However in some embodiments, the various fibers in the single bundle (trunk) at the first end can advantageously be subdivided into smaller bundles (e.g. a plurality of branches) to divert various portions of the light to two or more spectrometers. Depending on the application, different branches can convey distinct preselected fractions of the light from the trunk to different spectrometers. For example, in an embodiment one branch from the trunk fiber bundle can convey a first portion of the light to a broadband spectrometer operable to analyze a relatively wide spectral segment, and a different branch can convey a second portion of the light to a high dispersion spectrometer operable to measure minor concentrations and/or trace elements. Emissions from a plasma plume can thereby be simultaneously analyzed in various ways using spectrometers having distinct and/or complementary capabilities. For example, a spectrometer having a high speed gated detector, a spectrometer having a high speed intensified detector (i.e. an ICCD), a spectrometer having an electron multiplying charge coupled device (EMCCD), and/or a spectrometer having enhanced sensitivity and/or selectivity in particular wavelength regions and or at particular wavelengths, can all receive and analyze radiation from the same plasma plume carried through different branches. It will be understood that various advantageous spectrometer characteristics may not be exclusive. For example, a spectrometer can be configured with a type of detector particularly well suited to the characteristic light throughput (efficiency) and resolution of its dispersive element(s), as well as being selectively gateable to detect light exclusively in a preselected interval following each laser pulse. In particular, an intensified multichannel charge coupled device detector can be intensified to provide very high sensitivity relative sensitivity, and/or can be synchronously gated on during a short interval following each laser pulse to discriminate against background continuum radiation.

The terminology herein is for the purpose of describing particular embodiments and is not intended to be limiting of the invention. It will be understood that, although the terms first, second, etc. may be used to describe various elements, these terms are only used to distinguish one element from another, and the elements should not be limited by these terms. For example, a first element could be termed a second element, and similarly a second element could be termed a first element, without departing from the scope of the instant description. As used herein, the singular forms "a", "an" and "the" are intended to include the plural forms as well, unless the context clearly indicates otherwise. It will be further understood that the terms "comprises," "comprising," "includes," "including," and/or "having," as used herein, are open-ended terms of art that signify the presence of stated features, integers, steps, operations, elements, and/or components, but do not preclude the presence or addition of one or more other features, integers, steps, operations, elements, components, and/or groups thereof. Reference in the specification to "one embodiment", "an embodiment", or some embodiment, etc. means that a particular feature, structure, or characteristic described in connection with the embodiment is included in at least one embodiment. The appearances of the phrase "in one embodiment" in various places in the specification are not necessarily all referring to the same embodiment, nor are separate or alternative embodiments mutually exclusive of other embodiments.

As used here, various terms denoting spatial position such as above, below, upper, lower, leftmost, rightmost and the like are to be understood in a relative sense. The various aspects of the apparatuses described herein are operable without regard to the spatial orientation of the apparatuses as a whole. For example, an apparatus can be configured in a vertical orientation or in a horizontal orientation. Hence a component or module that is described as being above another component or module in a first embodiment having a first orientation, could equivalently be described as being to the left of the other component or module in an equivalent second embodiment configured to be in a second orientation 90 degrees counterclockwise with respect to the first.

The term module refers to a distinct unit that is operable to perform an identifiable function. A module can be a self-contained physical unit or piece of equipment. A module can also be a logical component effectuated by a processor and tangible media having instructions and/or data that are operable for the processor to perform the identifiable function. The term automatic refers to a module, service, or control system that is operable to perform with no human interaction. Monitoring or sensing refers to measuring a physical quantity. Monitoring is often performed for the purpose of regulation or control.

The term gas or gas phase species as used herein includes species not bound to each other that have thermal and/or directed motion in a gas phase. The term is not limited by a specific value of a mean free path between collisions. Hence the term "gas phase species" includes various different species in vapors, atomic or molecular beams, and gaseous suspensions such as aerosols, and the like.

A lightguide refers to a transmission channel for the directed transmission of luminous electromagnetic radiation over a distance. A lightguide can include one or more fine filamentary optical fibers comprised of dielectric material such as silicon dioxide, a transparent polymer, and the like. The outer surface of each individual optical fiber can have a cladding of relatively lower refractive index. A lightguide have a cross section that is circular, rectangular, U-shaped, ribbon-shaped, and others. The cross section can be solid or it can be hollow. By way of further example, a lightguide can be covered with a jacket comprised of transparent material, opaque material, and others.

The term spectrometer is generally used to identify an instrument that can used to view and/or analyze a characteristic of a substance. With reference to LIBS, an optical spectrometer (also referenced as "spectrometer") is an instrument operable to separate and detect different wavelength components in electromagnetic radiation within a range of about 180 nm to 1000 nm (ultraviolet to infrared). However, depending on the context, the term optical spectrometer ("spectrometer") can also be understood to mean the subsystem in an optical spectrometer operable to disperse and/or separate various wavelength components of the electromagnetic radiation (e.g. a monochromator or polychromator exclusive of an electromagnetic radiation detector). The intended meaning can be understood from the context.

The term a mass spectrometer (MS), as used herein, references an instrument that can separate and detect ions gas based on their charge to mass ratio. The term inductively coupled plasma mass spectrometer (ICP-MS) will be understood to mean an analysis instrument based on ionizing gaseous species in a high temperature inductively coupled (thermal) plasma, extracting such ionized species from the plasma, and determining their composition with a mass spectrometer.

The present teachings may be embodied in various different forms. In the following description, for purposes of explanation, numerous specific details are set forth in the description and drawings in order to provide a thorough understanding of the various principles. Furthermore, in various instances, structures and devices are described and/or drawn in simplified and/or block diagram form in order to avoid obscuring the concepts. However, it will be apparent to one skilled in the art that the principles can be practiced in various different forms without these specific details. Hence aspects of the invention should not be construed as being limited to the embodiments set forth herein.

FIG. 1 shows a schematic overview of a laser ablation apparatus 100 according to the present invention. The apparatus 100 generally includes a pulse laser 102, a stage 106, a position sensor 112, a spectrometer 120 and a system computer 140. The apparatus 100 is configured to generate laser pulses from the pulse laser 102. The laser pulses are focused onto a sample 105 with a lens 104 to produce a plasma plume 114 of the sample 105 at a sample site 110. The position sensor 112 is electrically coupled with the system computer 140 for sending a displacement error signal to automatically correct positioning of the stage 106 during an ablating process as describe further below. The apparatus 100 can include a system frame for housing the various components described herein. The system frame can include an air filter for filtering contaminants produced during the ablating process.

The pulse laser 102 in an exemplary embodiment comprises a neodymium doped yttrium aluminum garnet (Nd:YAG) laser for generating energy in the near infrared region of the electromagnetic spectrum with a wavelength of 1064 nm. The pulse duration can be approximately 4 ns for generating a laser beam with a power density that can exceed one GW/cm.sup.2 at a focal point or ablation impact point. The laser 102 can have a repetition rate of approximately 10 hz or alternately lower than 10 hz in some embodiments. Alternatively, the pulse duration can vary to tens or hundreds of nanoseconds. In another embodiment, the pulse duration can be shortened to ultra short femtoseconds. The lens 104 comprises an objective lens used to focus the laser beam on a surface of the sample site 110. The laser beam can be focused to a spot size of approximately 10-500 micrometers on the sample site 110. In an exemplary embodiment, the laser beam can be focused to a spot size of approximately 150-200 micrometers on the sample site 110.

In an alternative embodiment, a spark generator can be used as the ablation source instead of the pulse laser 102. An electric spark is passed through a sample material until the sample material reaches a temperature where characteristic spectral emissions can be detected. In an exemplary embodiment, the electric spark can be controlled in an argon atmosphere. A person of ordinary skill in the art can appreciate the construction of such spark generators in spark spectroscopy systems.

A dichroic mirror 107 is used for directing the laser beam toward the sample site 110 and a mirror 109 allows viewing of the sample site 110 using a video camera 116.

The stage 106 includes an attached array of 'x-y-z' motors 108 for providing translation of the stage 106 in a three dimensional space. The x-y-z motors can comprise suitable stepper motors driven by stepping motor controllers (not shown), as known by a person of skill in the art. In one embodiment, the stage 106 can have a translation rate of approximately 10 cm/s. The stage 106 can include a sample securing means.

Figure 1A:
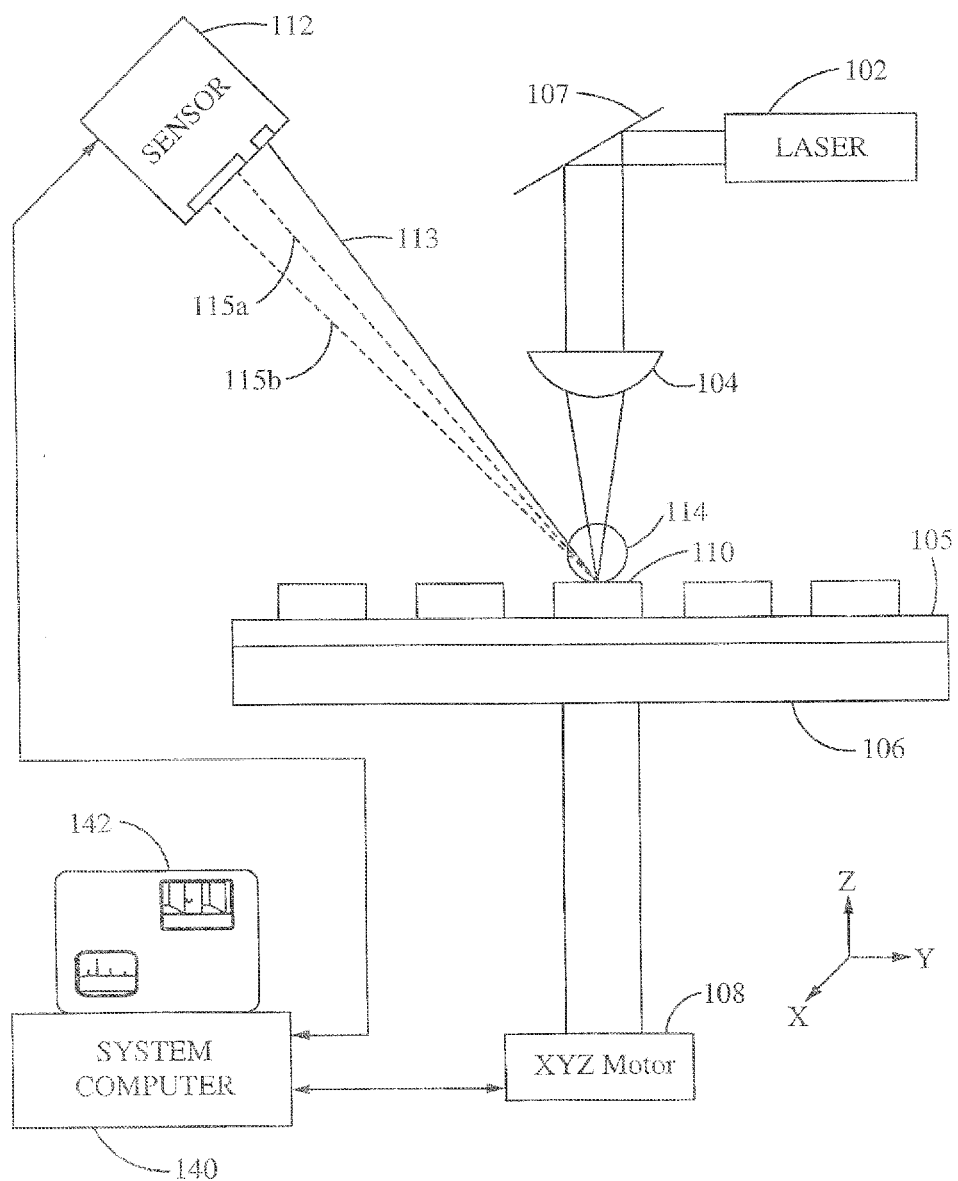
FIG. 1A is another diagram of a laser ablation apparatus embodiment.

The position sensor 112 preferably comprises a laser triangulation sensor. The position sensor 112 preferably uses the principle of triangulation to determine changes in height of the stage 106 and the associated sample 105. As shown in greater detail in FIG. 1A, triangulation occurs when the position sensor 112 emits a triangulation laser beam 113 that is focused on the sample site and a first reflection 115a is sensed by a photodetector within the position sensor 112. A change in height of the sample site 110 causes a displacement in the triangulation laser beam 113 to produce a second reflection 115b and a displacement signal generated by the position sensor 112 is communicated to a system computer 140. The system computer 140 provides positioning information to maintain an optimum height of the sample site. The position sensor 112 can comprise a suitable laser displacement measuring device as known to a person of skill in the art. In one embodiment, the triangulation laser 113 coincides with a spot circle of the laser 102 generated at the sample site. The triangulation laser 113 can also be used as a targeting marker when selecting a specific point on the sample site 110 as seen with the video camera 116 as the triangulation laser 113 can produce a visible spot on the surface of the sample site 110.

The spectrometer 120 (FIG. 1) collects electromagnetic information from the plasma plume 114. The spectrometer 120 can be a monochromator or a polychomator with a detector. The electromagnetic information includes spectral information identifying an elemental composition of the sample site 110. A spectral range for the spectrometer 120 can be chosen to suit different applications. In an exemplary embodiment the spectral range can be approximately 35 nm for observing a portion of the electromagnetic wavelength range. Alternatively, the spectrometer 120 can detect electromagnetic radiation in a range of 200 to 900 nm. Collection optics 122 receive light and plasma lumina generated from the plasma plume 114 and transmits the light and plasma lumina through a fiber cable 124 to the spectrometer 120. The collection optics 122 can be orientated horizontally as shown in FIG. 1. Alternatively, the collection optics 122 can be orientated at any angle above the sample 105 surface plane. A mirror (not shown) within the spectrometer 120 reflects the plasma lumina to a grating that disperses the plasma lumina.

An intensified charge coupled device (ICCD) or detector 130 is coupled with the spectrometer 120 for detecting the dispersed plasma lumina. The detector 130 provides the detected plasma lumina to the system computer 142. The system computer 140 generates spectral information from the plasma lumina of the laser plume 114. The spectral information includes intensity data representing elemental information and composition of the sample site 110. The spectral information can be produced on a display 142.

The detector 130 provides increased resolution and greater selectivity of the spectral information. The detector 130 includes a microchannel image intensifier plate. The intensifier plate is preferably gated during period of time when the plasma plume 114 emits characteristic atomic emission lines of the elements. This period coincides with an optimum plume luminance period. This period follows emission of continuum radiation. Continuum radiation lacks useful specific species or elemental information. In one embodiment, a delay generator (not shown) can be included to provided gating of the detector 130 to allow temporal resolution of the detector 130 response time. Alternative embodiments of the detector 130 can include a detector other than an ICCD, for example a suitable charge coupled device (CCD) or suitable photomultiplier. Accuracy of the spectrometer 120 and detector 130 in one embodiment can generate compositional data in the range of 20 ppm or less. Alternatively, the accuracy can be in the range of a few %. In another embodiment, the accuracy can be in the range of 1%, which is approximately 10,000 ppm.

The system computer 140 can include application software and a controller in the system computer 140 for providing synchronization of the laser 102, spectrometer 120, detector 130, position sensor 112 and the x-y-z motors 108 positioning of the stage 106. The system computer 140 is electrically coupled with the laser 102, spectrometer 120, detector 130, position sensor 112, the x-y-z motors 108 and the camera 116. The system computer 140 includes a display 142 for displaying spectral information. The system computer 140 can present the spectral data generated on the display 142. Alternatively, a separate personal computer can also be coupled with the system computer 140 for separately analyzing the spectral information. The system computer 140 can include a power controller to regulate power to all the apparatus 100 components.

The application software decodes the spectral information from the detector 130 and facilitates analysis of the spectral information and generates composition information of the sample 105. In one embodiment, the intensity data of an elemental peak is subtracted from background data of the elemental peak to calculate a change in intensity (delta I). The application software allows setting of certain parameters for performing the laser ablations of the sample site 110. A laser spot circle size can be set as a parameter and can be consistently and precisely maintained through the laser ablation process described in further detail below. Alternatively, a z value for the sample site 110 can be set as a parameter and can be consistently and precisely maintained through the laser ablation process. The spot circle increases or decreases depending on the change in height of the sample site 110. Keeping the laser 102 spot circle precisely adjusted insures that the sample site 110 produces the plasma plume 114 with consistent optimum plume luminance. Height changes in the sample site can be detected by the position sensor 112 and a correction to the height of the sample site 110 is generated by the controller within the system computer 140. The application software and the controller generate correction signals to reposition the height of the stage 105 after each laser ablation of the sample site.

Figure 2:
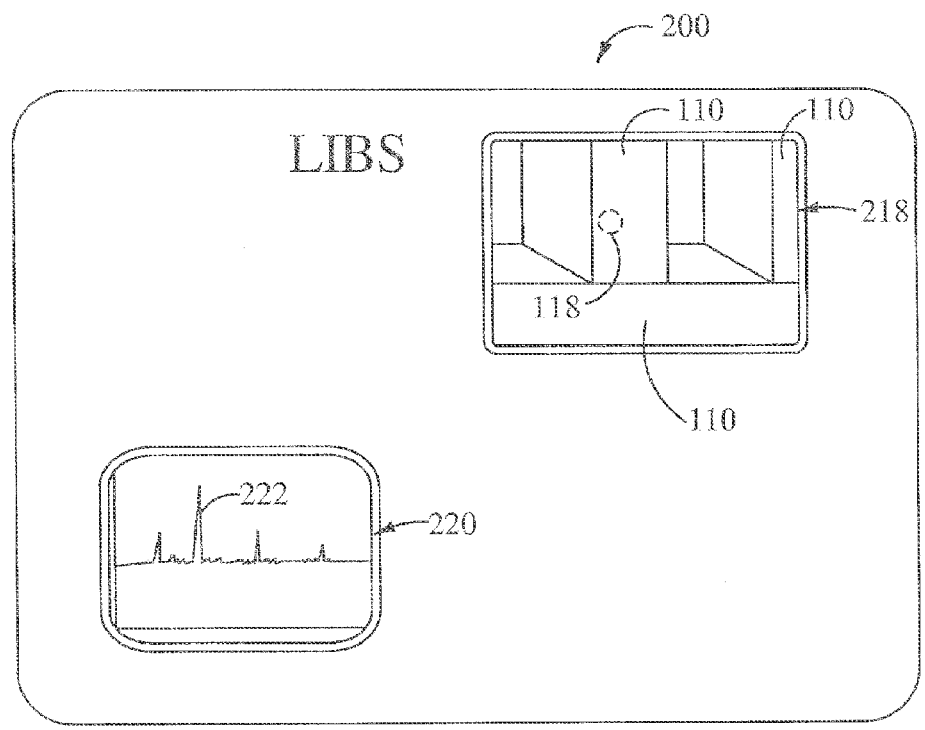
FIG. 2 illustrates a detail of a laser ablation graphical user interface.

FIG. 2 shows a representative graphical user interface (GUI) 200 according to an embodiment of the present invention. The GUI 200 includes a first data window 218 and a second data window 220. The first data window 218 provides real-time video of a sample site 110. A spot circle 118 can be observed on the sample site 110 during and following an ablation. The second data window 220 provides spectral information generated from the system computer 140. In an exemplary embodiment, the spectral information includes a waveform 222 representing intensity and wavelength data of a sample site ablation.

Figure 3:
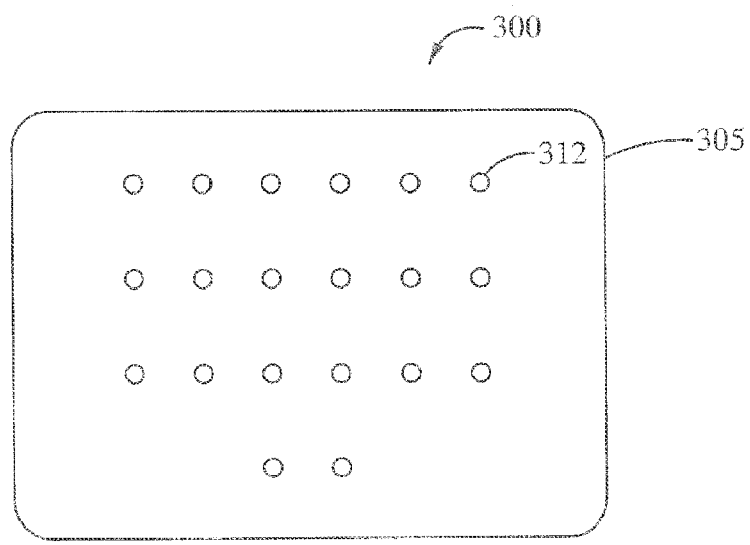
FIG. 3 illustrates a plan view of a testing protocol.

FIG. 3 shows a top view 300 of a protocol for ablating a sample 305 according to an embodiment of the present invention. The protocol includes ablating multiple sample sites 312. In an exemplary embodiment, the sample sites can be uniformly and evenly distributed throughout a surface of the sample 305. Alternatively, the sample sites 312 can be randomly distributed through the surface of the sample site. The number of sample sites 312 ablated can vary depending on a particular sample or a particular application. In one embodiment, the number of sample sites comprises twenty. Alternatively, the number of sample sites can be ten or fewer. In another embodiment, the number of sample sites can be thirty or more.

The protocol 300 can include a specific number of pulse laser ablations per sample site 312. Heterogeneous material can include elements having varying thermal properties. A single shot laser ablation can vaporize disproportionately more volatile elements than the less volatile elements. Spectral information from a single ablation may not be a reliable indication of the composition of the sample 305. In an exemplary embodiment, the number of laser ablations per site comprises three laser ablations. Alternatively, the number of laser ablations per site comprises two. In another embodiment, the number of laser ablations per site comprises a single laser ablation. In still another embodiment, the number of laser ablations per site comprises four or more laser ablations.

Figure 4A:
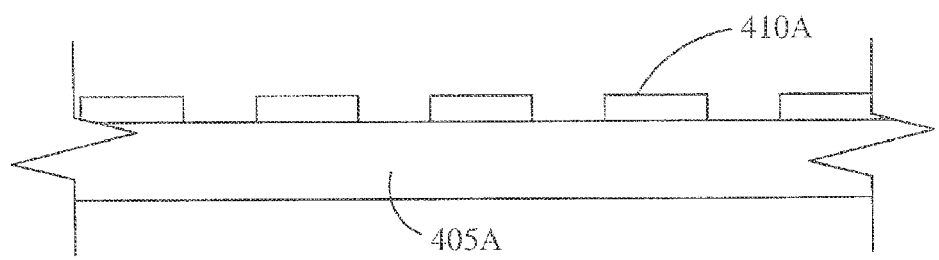
FIGS. 4A and 4B illustrate side views of a topology of a sample according to an embodiment.
Figure 4B:
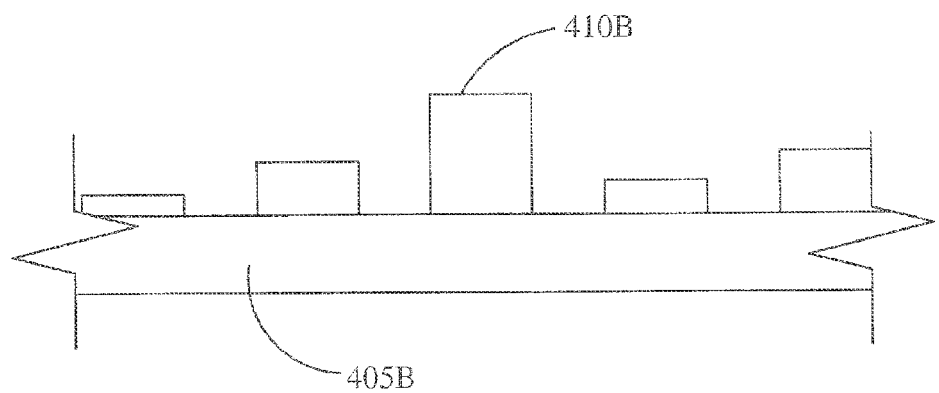

FIGS. 4A and 4B show side views of a first sample 405A and a second sample 405B according to an embodiment of the present invention. The first sample 405A comprises a material having sample sites 410A with substantially uniform topology. The height of the sample sites 410A are substantially the same. The second sample 405B, however, comprises a material having sample sites 410B with erratic or varying topology. The height of the sample sites 410B can be different. The apparatus 100 is configured to provide consistent spectral data for either the uniform sample sites 410A or sample sites 410B with varying heights. The system computer 140 adjusts the height of the stage 106 to achieve the optimal plasma lumina.

Figure 5:
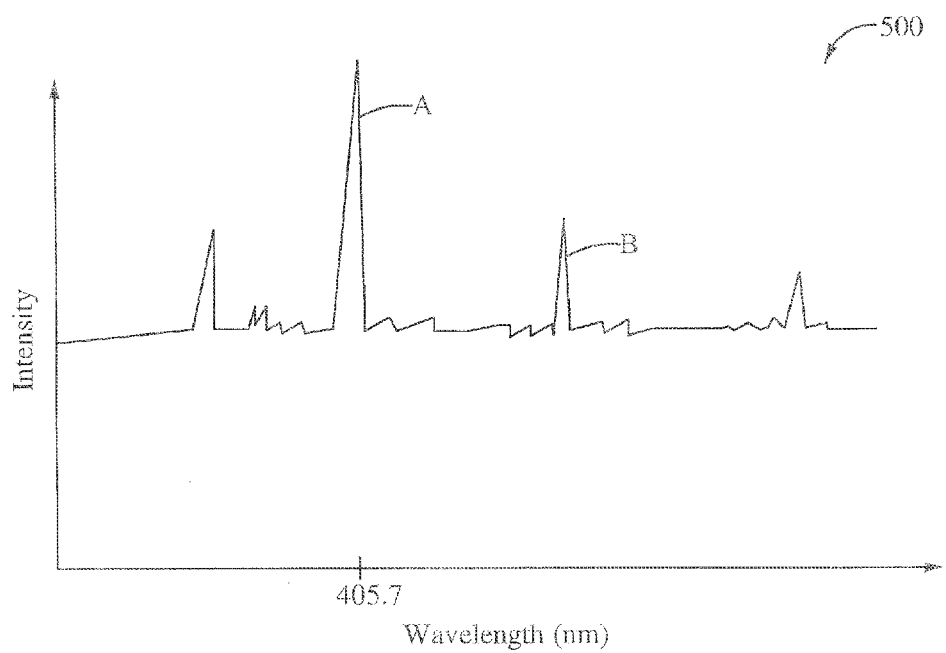
FIG. 5 illustrates a plot of spectral information according to an embodiment.

FIG. 5 shows a plot 500 of spectral data according to an embodiment of the present invention. The plot 500 includes a waveform plotted along a wavelength (nm) versus an intensity (a.u.). An elemental peak 'A' can represent the spectral information for the element Lead (Pb). The elemental peak 'B' can represent spectral information of a different element.

Figure 6:
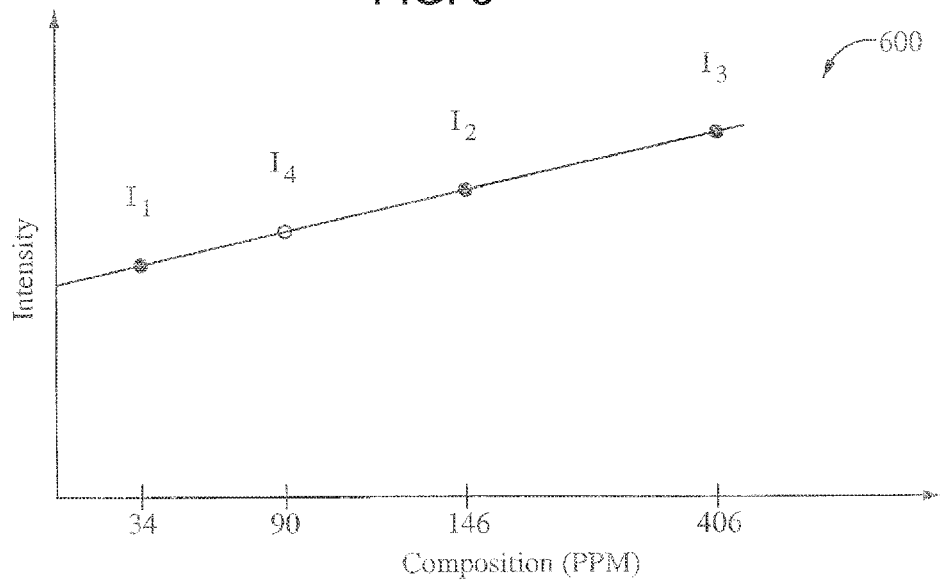
FIG. 6 illustrates a plot of intensities of known standards according to an embodiment.

FIG. 6 shows a plot 600 of compositional data 600 according to an embodiment of the present invention. The plot 600 includes a waveform plotted along a composition (nm) versus an intensity (a.u.). The plot 600 is generated by performing laser ablation according to the method described herein on a known standard sample. The known standard produces intensities I1, I2 and I3 for associated elements at the respective compositions 34 ppm, 146 ppm and 406 ppm. Quantitative analysis of different elements of a particular sample is performed by comparing spectral data of the particular sample with the compositional data 600. For example, spectral information obtained from analysis with the apparatus 100 can include intensity I4. The quantity of the element can be approximated to 90 ppm.

Figure 7:
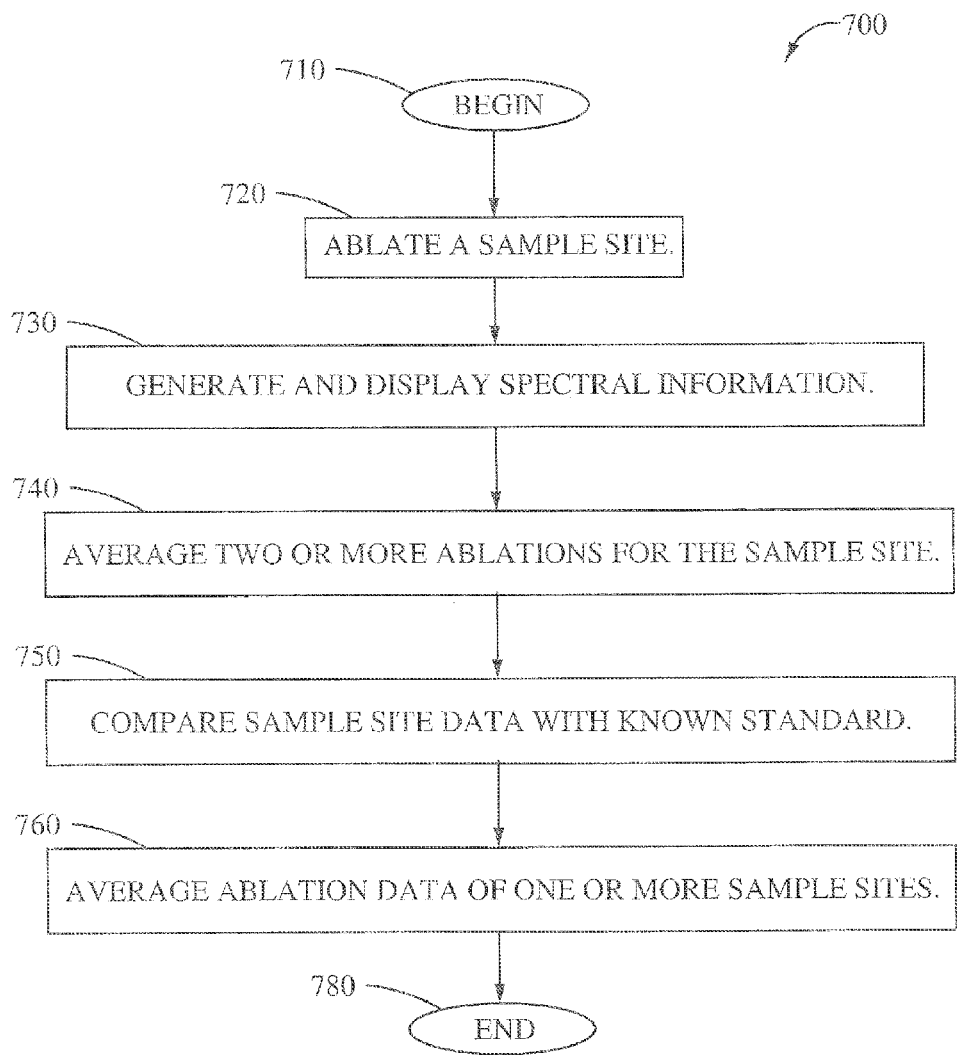
FIG. 7 illustrates a process flow diagram for a method of ablating.

FIG. 7 shows a process flow diagram for a method 700 of laser spectroscopy according to an embodiment of the present invention. The laser ablation apparatus 100 (FIG. 1) is used as an example. The method 700 begins at the step 710. In one embodiment, the method 700 can be fully automated using application software included in the system computer 140. A specific protocol can be entered into the application software instructing the application software of desired parameters or settings for the apparatus 100. Alternatively, the method 700 can be manually performed. At the step 720, a laser pulse is generated to ablate the sample site 110 into an emissive plasma plume. A real-time video image of the sample site 110 is generated on a first window 218 of the GUI 200. The real-time video is received from the video camera 116. The plasma plume 114 is analyzed by the spectrometer 120 and the detector 130. The plasma lumina and the electromagnetic radiation generated by the plasma plume is optically communicated to the spectrometer 120 and detected by the detector 130. The position sensor 112 provides a displacement signal to the system computer 140 indicating any change in the height of the sample site 110. The system computer receives spectral information from the spectrometer 120 and the detector 130.

At the step 730, the system computer 140 generates spectral and wavelength information for presentation on the display 142. In one embodiment, intensity and wavelength data are represented as waveforms on the GUI 200. The waveform is presented in a second window 220 of the GUI 200 and includes the intensity and wavelength data. In another embodiment, a second waveform is superimposed on the first waveform 222 in the second window 220. The second waveform can include additional spectral information. For example, particle imaging information, tracking information or scaled or gated representations of the first waveform 222.

At the step 740, the steps 720 and 730 are repeated for each sample site on the sample. The spectral data for a total number of laser ablations for the sample site 110 can be averaged together. In an exemplary embodiment, the total number of laser ablations for the sample site 110 equals three laser ablations. The spectral data of the three laser ablations are averaged together to generate a 'site sum'. The site sum is a reliable and accurate representation of the elemental composition of the sample 105 at the sample site 110. Alternatively, the site sum comprises spectral data from two laser ablations. In another embodiment, the site sum comprises spectral data from one laser ablation. In still another embodiment, the site sum comprises spectral data from four or more laser ablations.

At the step 750, the site sum can be compared with spectral information generated from performing the method described herein on a known standard material. The known standard material comprises specific known elements at a known composition. Laser spectroscopy performed on the known elements generates known spectral data including known intensity values. An elemental composition for the sample site 110 can be approximated by comparing the site sum with the known standard spectral data.

At the step 760, the steps 720 through 750 can be repeated for one or more additional sample sites to generate additional site sums. The spectral data for the total number of site sums can then be averaged together. In an exemplary embodiment, the total number of site sums equals twenty. The spectral data of the twenty site sums can be averaged together to generate a 'sample sum'. The sample sum is a reliable and accurate representation of the elemental composition of the sample 105 as a whole. Alternatively, the total number of sites sums can be ten or fewer. In another embodiment, the number of sites sums can be thirty or more.

The apparatus 100 can perform laser ablation or laser induced breakdown spectroscopy (LIBS) on a variety of materials. The materials can be heterogeneous or homogeneous solids or semi-solids. Alternatively, the materials can comprise a liquid or even a gas. In another embodiment, the apparatus 100 can be used for LIBS on biological materials. Analysis of biological material can include building a library of known spectral signatures including elemental and compositional data for specific biological material. The spectrometer 120 can collect and detect with the detector 130 spectral information on a broad range from 200 to 900 nm. An unknown biological sample can be compared with the library to determine the biological substance. The method ends at the step 780.

In an alternative embodiment, the method 700 can be used in a remote configuration. The sample material is positioned in a location that is remote from the ablation source or laser. A telescopic device can be integrated with the apparatus 100 to provide optical coupling of plasma lumina. The generation and analysis of spectral data can proceed similarly as described herein. Furthermore, other spectroscopies, in place of and/or in addition to optical emission spectroscopies can be used to obtain characteristic ablation spectral data within the scope of the present invention. For example, laser ablation inductively coupled plasma mass spectrometry (LA-ICP-MS) can be applied in conjunction with and/or as an alternative to the LIBS technique described herein.

Still further embodiments can be understood with respect to FIGS. 8-13B. Like numerals in FIGS. 8-13B designate corresponding elements.

Figure 8:
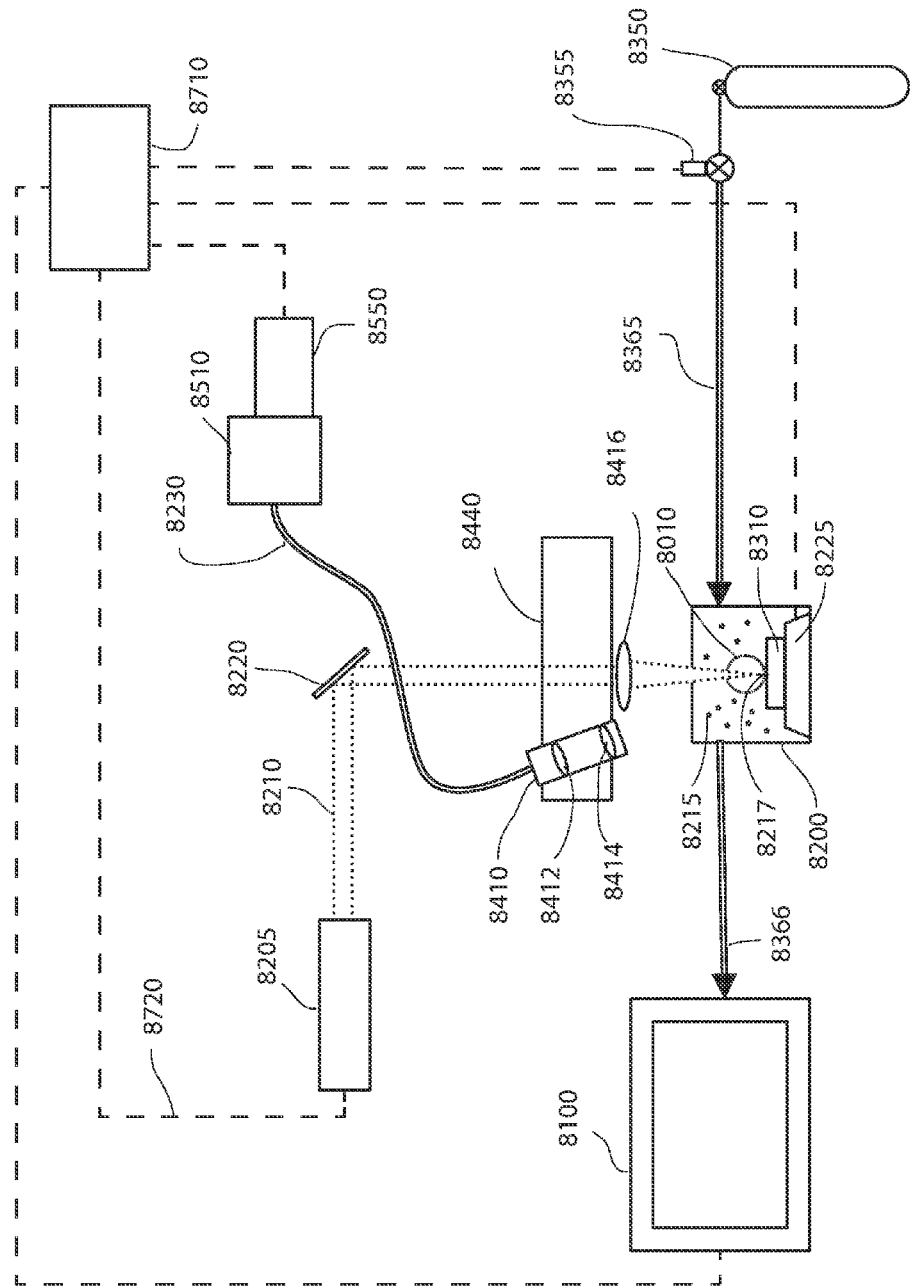
FIG. 8 is a simplified diagram of apparatus for laser induced ablation spectral analysis including LIBS and LA-ICP-MS.

FIG. 8 is a simplified drawing of a system for laser induced ablation spectral analysis of a sample. The system has a movable stage 8225 coupled to x-y-x translation motors (not shown) that can move a sample 8310 on the stage in three independent directions. The system also has a laser 8205 that can emit a pulsed laser beam 8210, and has various optical elements such as a mirror 8220, laser beam focusing optics module 8416 and/or others that can cooperatively focus the laser beam onto a selected sample site 8217 for ablation. The sample 8310 and stage can be in an unreactive gaseous atmosphere confined within enclosure 8200. The atmosphere in the enclosure can be transparent at wavelengths comprising pulsed laser beam and/or characteristic spectral emission emanating from the plasma plume 8010. In a preferred embodiment, the pulsed laser 8205 can be a Nd YAG laser emitting a pulsed laser beam with a near infrared wavelength of 1064 nm, and the unreactive atmosphere can be inert gas such as helium and/or argon.

However an ultraviolet wavelength selected from among 193 nm, 266 nm and 193 nm is preferred for the ablation for some applications, particularly when performing analyses using ICP-MS. UV wavelengths can provide a better sample of gaseous species from a sample site by comparison to a more conventional pulsed laser wavelength in the near infrared. Short UV wavelengths can be generated as harmonics of longer wavelength exicimer and/or solid state lasers as will be understood by those having ordinary skill in the art.

Figure 12A:
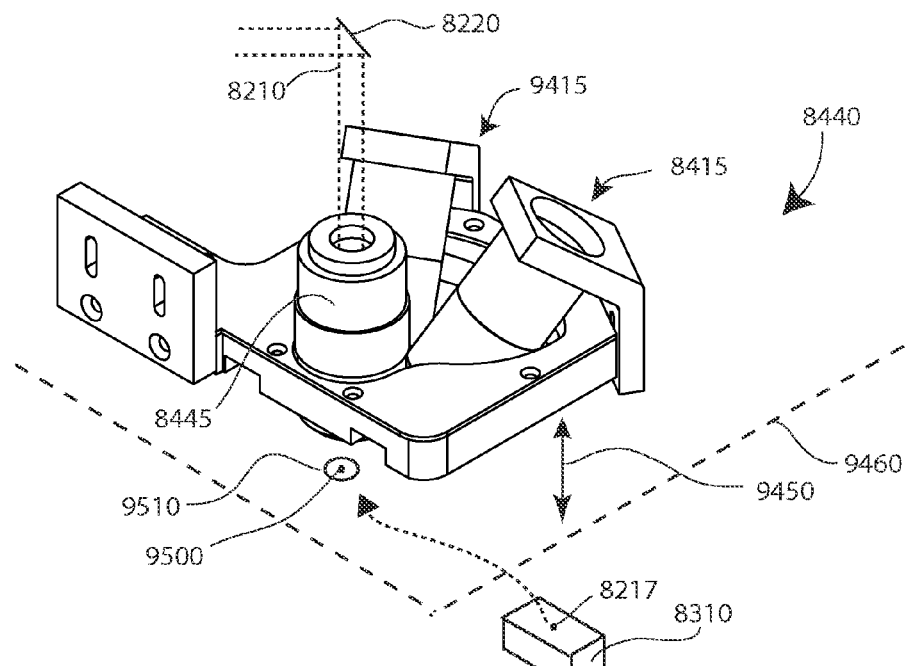
FIG. 12A is an isometric view of an optical frame for an LIBS apparatus.
Figure 12B:
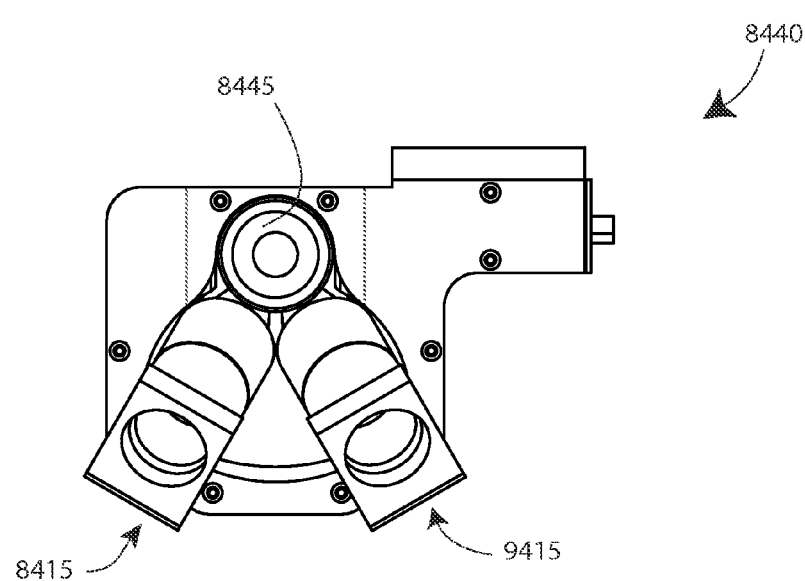
FIG. 12B is an overhead view of the optical frame shown in FIG. 12A.

Characteristic spectral emission emanating from the plasma plume 8010 generated by ablation can be gathered with a collection optics module 8410. The collection optics module can couple the spectral emission into a lightguide 8230. The lightguide can transmit the optical emission to an optical spectrometer comprising wavelength separation unit 8510 and detector 8550. The collection optics module can include lenses 8412, 8414 and/or other optical elements and is disposed in a preselected position and orientation by optical frame 8440. Further details of an optical frame structure 8440 are disclosed in FIGS. 12A, 12B and 13. As shown in FIG. 12A, the laser beam focusing optics module 8445 is secured to frame 8440 in a position where it can center a precise laser spot circle 9510 of predetermined size in plane 9460 on a point 9500. Plane 9460 is a preselected distance 9450 below optical frame 8440. Accordingly, stage 8225 can movably translate a selected sample site 8217 (also see FIGS. 9-10) to the center laser spot circle position to perform precise and consistent laser ablation of material from the selected site.

As can be understood with respect to FIGS. 10-13, the optical frame 8440 has support substructures 8415, 9415 operable to secure collection optics modules 8410 and/or 9410 in a preselected positions with respective central axis/axes 8416 and/or 9416 of each collection optics module aimed at a situs 9300 of the plasma plume. This arrangement positions each laser ablation and its ensuing plasma plume in the same location relative to the optics support structure 8440. Accordingly, each optics support substructure 8415, 9415 can hold a respective collection optics module 8410, 9410 in a fixed position and orientation that can optimize light collection from a plasma plume arising from the spot circle position.

In various embodiments, a gas flow system such as shown with respect to FIG. 8 can maintain an atmosphere of unreactive carrier gas in sample/stage enclosure 8200. A source of pressurized unreactive gas 8350 can be coupled to a flow controller 8355 through a fluid channel comprised of conventional tubing, pipe and/or fittings. The flow controller 8355 can deliver a selected flow rate of the carrier gas to enclosure 8200 through fluid passage 8365. Flow controller 8355 can be a pneumatic flow controller, an electronic mass flow controller, a fixed orifice, and others. The flow rate can be controlled using a computer 8710 to actuate the flow controller and/or provide a setpoint by way of a communication channel represented by the dashed line between a computer 8710 and flow controller 8355.

In some embodiments, gaseous laser ablation products 8215 generated in chamber 8200 can be transported in the carrier gas from enclosure 8200 to an inductively coupled plasma-mass spectrometer (ICP-MS) 8100 through flow channel 8366. In various embodiments, the gaseous laser ablation products can include permanent gases, vapors, molecular clusters, suspended particles, aerosols and/or others. The inductively coupled plasma-mass spectrometer (ICP-MS) 8100 is operable to perform a further spectral analysis of the ablation products based on the mass of ionized species. In various embodiments, the ICP-MS comprises an inductively coupled thermal plasma sustained in an inert carrier gas such as argon. Those having ordinary skill in the art will recognize that thermal plasma sustained in the ICP-MS 8100 have sufficiently high temperature (over 5000K) to ionize the gaseous laser ablation products. Ionized products from the thermal plasma are introduced into a mass analyzer within the ICP-MS where they can be separated and identified based on characteristic charge to mass ratio. Accordingly, the ICP-MS analysis can provide additional information useful to augment, improve, and/or confirm an emission spectroscopy determination of sample site composition based on lumina from the plasma plume.

It has also been found that ICP-MS may not be particularly effective to determine relative relatively light elements (atomic number less than about 10) and elements generally found in organic compounds (carbon, hydrogen, oxygen and nitrogen). In this regard, it has been found that the LIBS analysis can complement and quantify the concentrations of various elements that may not be acceptably measured using ICP-MS alone. Furthermore, it is difficult to measure high concentrations of elements (bulk composition analysis) in an ICP-MS while simultaneously performing trace level chemical analysis with the same instrument. On the other hand ICP-MS is highly sensitive and can perform trace level detection/analysis at levels as low as 1 part per billion, and under some circumstances even lower levels are operable. It has been found that a combination of laser ablation emission spectroscopy and laser ablation ICP-MS can determine both high concentration level analysis as well as trace levels at 1 ppm or even 1 ppb of a single sample site, which could not be performed using either laser ablation emission spectroscopy or laser ablation ICP-MS alone. Yet another advantage having both techniques in combination arises from an ability to detect pulse-to-pulse variations in the amount of ablated material based on a signal level in from wideband emission spectra. The emission signals can be useful to normalize and/or correct the ICP-MS mass/charge intensities thereby improving accuracy.

A system with respect to FIG. 8 can include at least one computer 8710. The computer comprises machine readable media operable to store data and instructions and a processor that can read the data and perform the instructions. Furthermore, media has various modules operable to effectuate various control functions, control loops, displays, human interfaces, and others. The dashed lines 8720 shown in FIG. 8 represent communications channels between the computer and various system components such as pulsed laser 8205, ICP-MS 8100, an optical spectrometer wavelength separation unit 8510, a spectrometer detector 8550, an electronic flow controller 8355, and a stage position controller for x-y-z stage 8255. The system can also include communications channels for a sample site position sensor, and other physical and/or software components not shown in FIG. 8. It will be recognized that a communication channel can be implemented in various different ways. For example, data and/or instructions can be carried by way of physical media as point to point wiring, over a parallel bus, over serial and/or parallel fiber optic connections, with a virtual circuit in a network protocol layer, and/or others.

It will be understood that various embodiments with respect to FIG. 8 can further include a number of additional elements and structures disclosed in relation to FIGS. 1-7 above. These elements are been omitted from the drawing to avoid obscuring other concepts simplify the explanation. By way of example, a system with respect to FIG. 8 can include a video camera, a sample site position sensor and an x-y-z stage position controller in a stage position control circuit, a triangulation laser, and others. Furthermore, some embodiments do not include all of the elements and subsystems shown. For example, there are embodiments with an ICP-MS. In these embodiments unreactive carrier gas from enclosure 8200 can be vented into an exhaust line (not shown).

Figure 9:
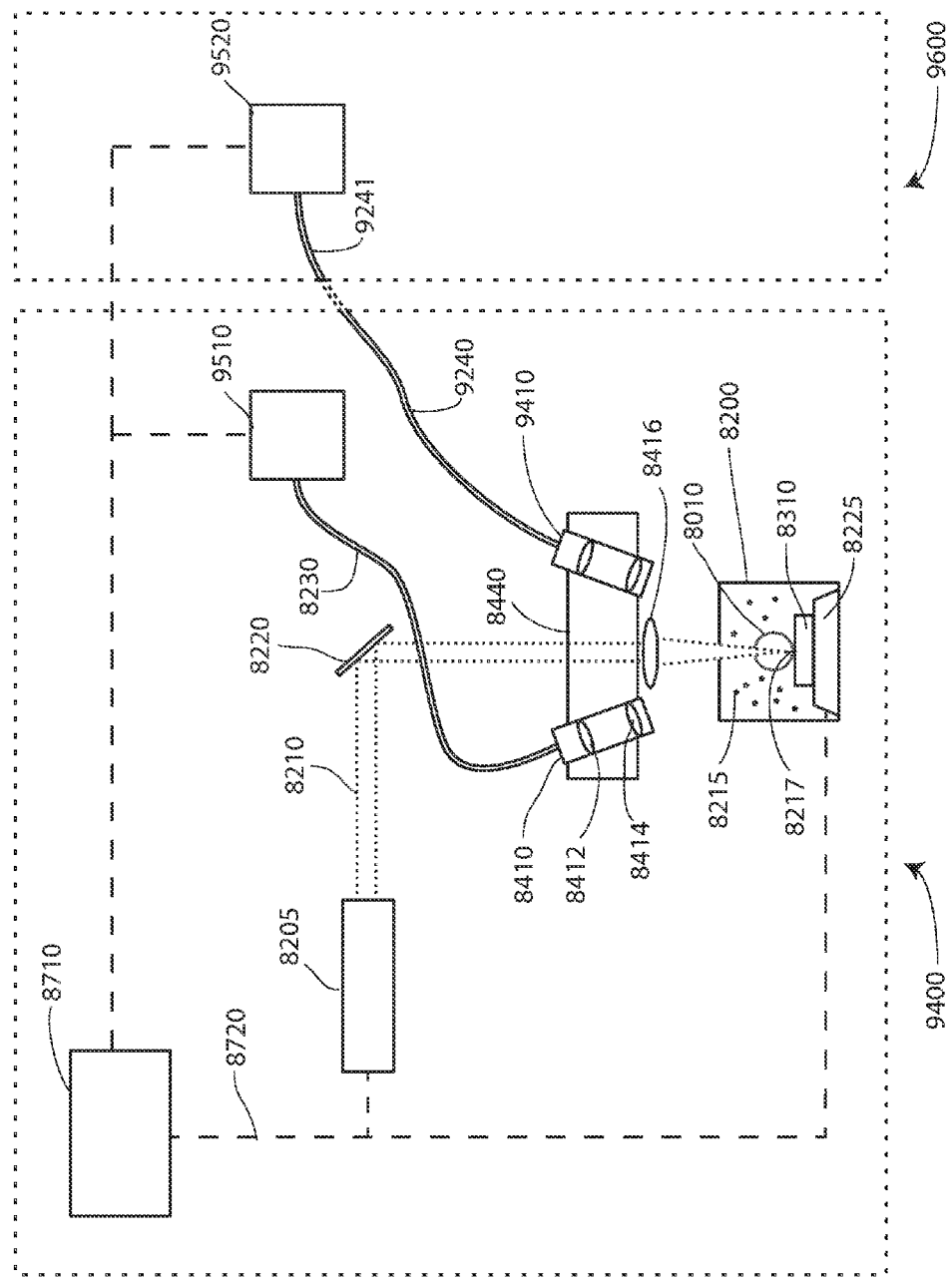
FIG. 9 is a simplified diagram of apparatus for laser induced ablation spectroscopic analysis comprising collection optics modules and fiber bundles to couple optical emission to spectrometers.

Other embodiments of a system for material analysis using LIBS can be understood with respect to the simplified diagram in FIG. 9. A system with respect to FIG. 9 comprises a master system module 9400, and can have an optional extension spectrometer module 9600. The master system module 9400 can include any of the elements and/or structures disclosed with respect to FIG. 8, including elements not shown in FIG. 9 (e.g. the carrier gas components 8350, 8355, and others are omitted for clarity). The optical frame 8440 of master unit 9400 is operable to support a second collection optics module 9410. The second collection optics module can gather spectral emission from a plasma plume 8010 and couple the light into a second lightguide 9240. Lightguide segment 9241 can deliver spectral emission to extension spectrometer 9600. In some embodiments lightguide segment 9240 in the master module and segment 9241 in the extension spectromter module can be portions of one single continuous fiber. In further embodiments, segments 9240 and 9240 can be physically different fibers optically joined through an interface connection between the master module and the extension spectrometer module.

An operable system with respect to FIG. 9 can comprise a master system module without any extension spectrometer 9520 (master only). The master only configuration can perform laser ablation optical spectroscopy using spectrometer 9510. Furthermore, a master only system can be field reconfigured to add an extension module. An extension model upgrade can add the capability to acquire emission spectra from a plume from the master system module spectrometer 9510 and extension spectrometer 9520 simultaneously. Spectral data from similar and/or different types of detectors in spectrometers 9510 and 9520 can be communicated to computer 8710 through communication channels 8720. A collection optics module 9410 to acquire plasma plume light emission for the extension spectrometer module 9600 can be included in master unit module 9400 when it is shipped from the factory, or a second collection optics module module 9410 can added to an optical frame 8440 in the field. Various embodiments with respect to FIG. 9 comprise an optical frame 8440 having collection optics module support substructures 8415, 9425, shown with respect to IGS. 12A, 12B and 13, to hold respective collection optics modules 8410 and 9410 in a preselected positions and orientations as shown.

Figure 13:
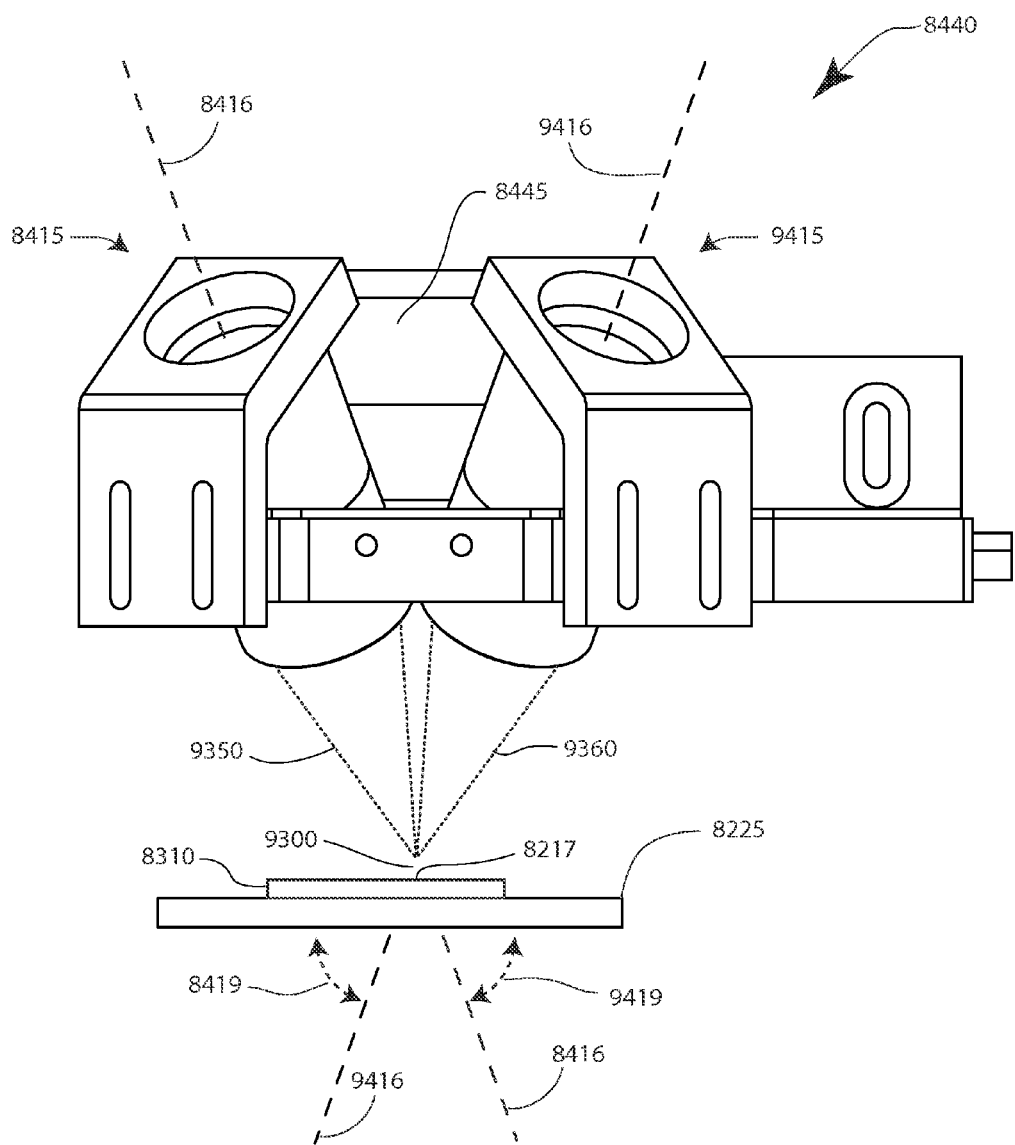
FIG. 13 is a side view of the optical frame shown in FIGS. 12A and 12B.

As shown with in FIG. 13, the supporting substructures 8415 and 9415 can have mirror symmetry with respect one another to be in predetermined positions directing the central axis 8416, 9416 of each collection optics modules to a point 9300 equidistant from each module, where the pulsed laser 8205 spot circle can generate a precise plasma plume. The central axes 8416, 9416 intersect an x-y plane parallel to the stage at equal angles 8419, 9419, from which each module can view from a plume at 9300 and capture equal portions of the light through equal solid angle cones 9350, 9360 subtended by the collection optics modules.

Figure 10:
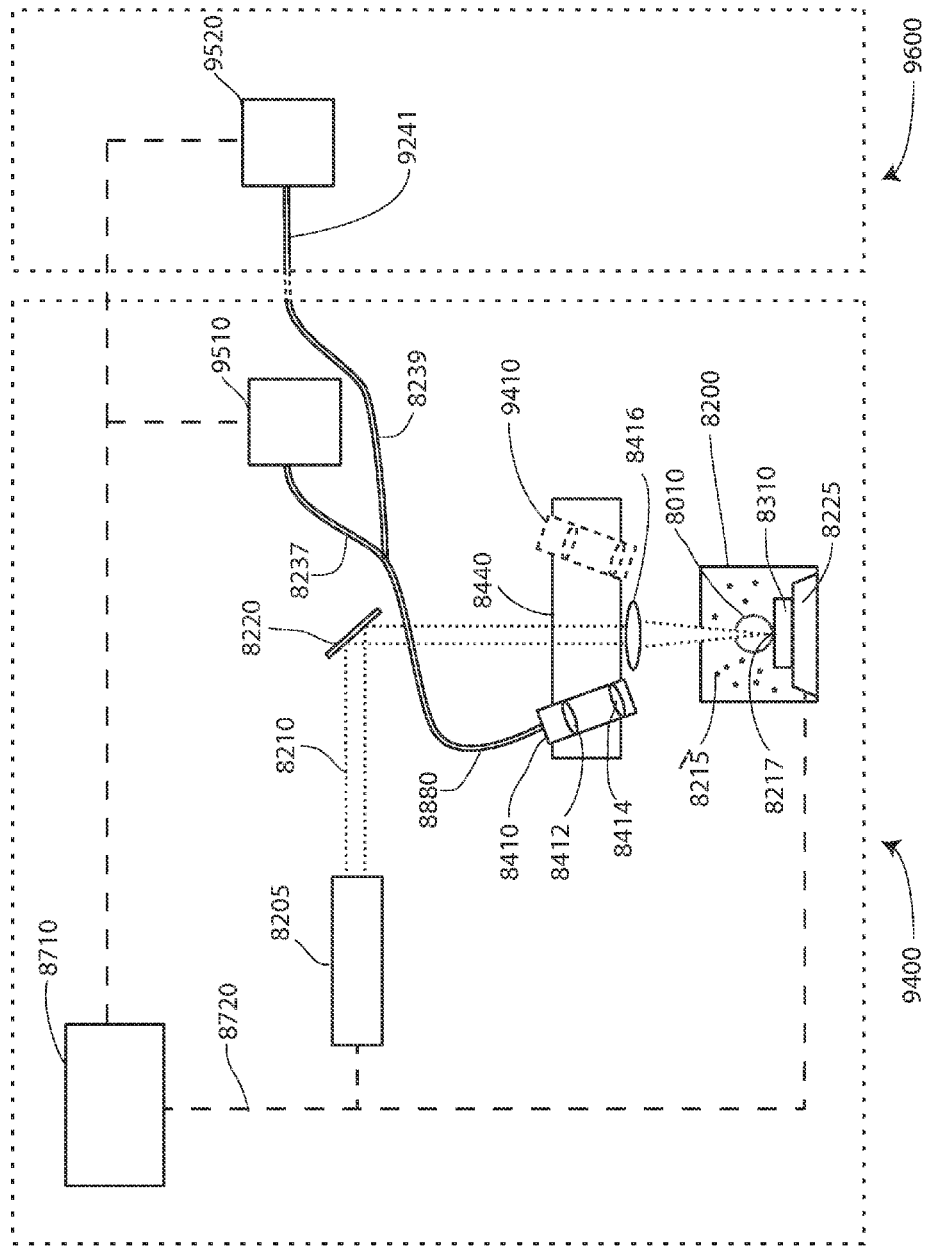
FIG. 10 is a simplified diagram showing an apparatus for LIBS having optical collection modules and lightguides for an internal and optional spectrometer modules.
Figure 11:
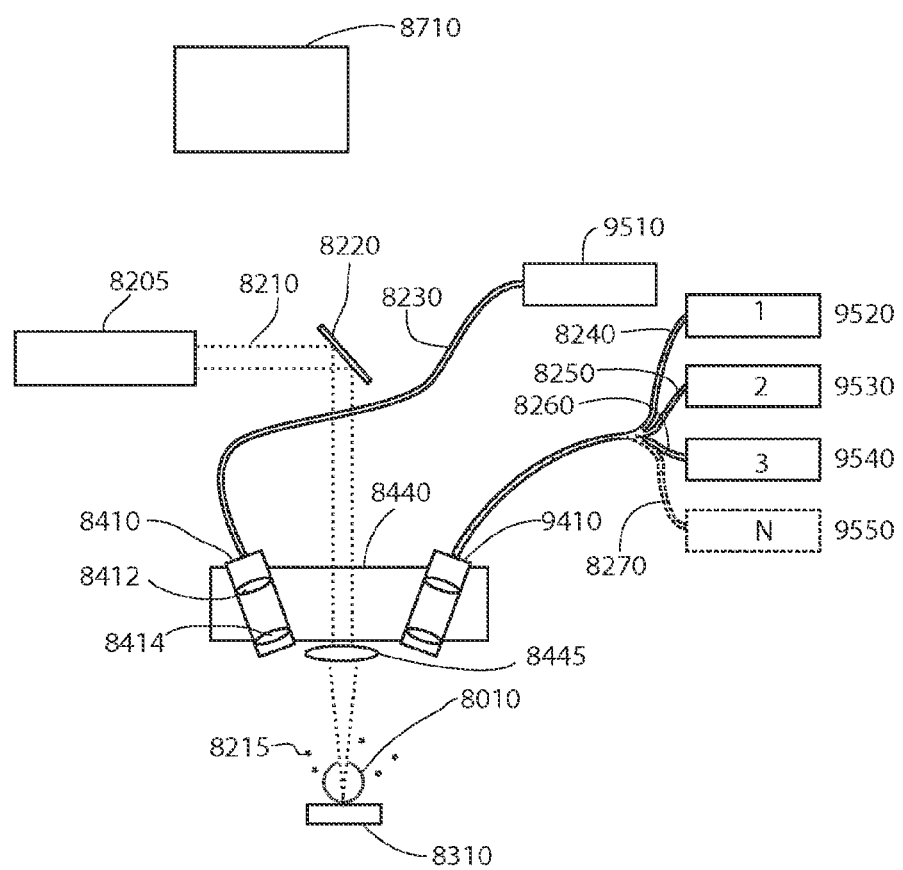
FIG. 11 is a simplified diagram of apparatus for laser induced ablation spectroscopic analysis for LIBS having one optical collection module coupled to an optical fiber bundle having split ends for an internal spectrometer and an optional spectrometer module.

In various other embodiments, a master system module can include one or more of the additional spectrometers and structures shown in an extension module with respect to 9-11 (e.g. a single master module LIBS system can comprise various spectrometers, lightgudes (optical fibers), and others disclosed with respect to FIGS. 9-11), within one physical unit (the instrument).

Some further LIBS system embodiments can be understood respect to FIG. 10. A lightguide fiber optic bundle 8880 connected to collection optics module 8410 can have a bundle of equal diameter fibers at a principal (proximal) end that is subdivided into smaller bundles leading to the distal split ends 8237 and 8239. Each of the distal split ends can illuminate a separate spectrometer 9510, 9520.

Furthermore, each of the distal split end bundle portions 8237, 8239 can have different numbers of fibers. Accordingly, luminous flux received from a collection optics module by the proximal end can be divided among the split distal ends in proportion to the number of fibers constituting each split end branch. In various embodiments relative to FIG. 10, total spectral power entering the proximal principal end of fiber bundle 8880 from collection optics module 8410, can be split to deliver a relatively smaller portion of the total power through a split end bundle 8237 comprising a relatively smaller number of fibers, and can deliver a relatively larger portion of the total power through a split end bundle 8239 comprising a relative larger number of fibers. The smaller portion of power can be delivered to a high sensitivity and/or low efficiency spectrometer 9510, and the larger portion of the power can be delivered to a low sensitivity and/or low efficiency spectrometer 9520. It will be appreciated that splitting total power in this manner can provide relatively more illumination where more power is necessary and/or desired, and relatively less illumination can be directed to a spectrometer where light intensity from the collection optics module might otherwise saturate its detector.

Relative to systems having two independent collection modules and two independent lightguides disclosed with respect to FIG. 9, use of a spit end lightguide, and/or split end lightguide optical power distribution system distribution (FIG. 10) can save the costs associated of a second collection module 9410 and/or second collection module support structure elements on the optical frame 8440.

Still further embodiments are disclosed relative to FIG. 11. A system with respect to FIG. 11 can provide a first collection optics module 8410 configured to couple a maximum portion of acquired luminous power to spectrometer 9510 through lightguide 8230. Various embodiments can also have a collection optics module 9410 coupled to the proximal principal end of an n-way split end fiber optic bundle. Each split end branch can convey spectral emission to a separate spectrometer. An embodiment with respect to FIG. 11 comprises a fiber lightguide assembly having 4 distal split end bundles 8240, 8250, 8260, 8270 configured to couple to respectively different spectrometers 9520, 9530, 9540 9550. Various further embodiments can have N different spectrometers coupled to a collection optics module with using an N-way split end fiber optic lightguide. There are also embodiments having a plurality of collections optics, where at least two of the modules are coupled to first and second pluralities of different spectrometers (e.g. N and M) using N-way and M-way split end fiber optic lightguides. In this regard, all of the spectrometers in system embodiments disclosed herein can be operable to simultaneous receive the spectral emission emanating from each plasma plume generated in a laser ablation of a sample site.

An LIBS system with the capacity to analyze the spectral emission from the plasma plume at an ablation site in real time, using a plurality of optical spectrometers to receive spectral emission simultaneously, and/or in tandem, has many advantages that enable superior analytical capability relative to prior art systems. Wavelength separating elements (monochromators, polychromators, filters, and others) as well as the detectors (i.e. CCD, ICCD, EMCCD, silicon photodiodes, photomultipliers, and others) useful in an optical spectrometer have absolute and spectral sensitivity limitations that can make it impractical and/or impossible to have sufficiently high spectral resolution, sensitivity, spectral bandwidth, and temporal resolution in a single optical spectrometer instrument that is operable to broadly determine a composition of unknown samples by LIBS multiwavelength analysis in real time. However, an individual spectrometer can be optimized to enhance sensitivity, resolution, and/or temporal resolution over limited range wavelengths. Accordingly, a plurality of optical spectrometers, individual selected and/or tuned to have optimal characteristics in a limited wavelength region, can provide spectroscopic analyses that are beyond capability of a single spectrometer system.

Analysis of a sample site by optical emission spectroscopy of the ablation plasma plume also can be limited by inherent characteristics of the plasma plume itself. For example, continuum emission can obscure characteristic spectral lines emanating from the ablated material from a sample site. As already disclosed above, continuum interference can be diminished and/or eliminated by using a high speed detector that is gated to exclusively detect line emission during a time interval after continuum intensity has decayed. Nevertheless, there are also inherent limitations arising from spectral overlap, interference, broadening, and/or low emission intensity at certain characteristic wavelengths, that remain difficult and/or impractical to overcome. Emission spectra analysis has some limitations can be traversed by applying a different spectral technology. For example, an ICP-MS can perform elemental and/or isotopic composition analyses at material concentrations well below 500 ppb, or even less than 1 ppb, that are inaccessible using emission spectroscopy alone. In various embodiments with respect to FIG. 8 simultaneous analysis of gaseous species from a sample site using ICP-MS can provide complementary ion mass to charge ratio peak intensity analytical information. In various embodiments, computer 8710 has analytical software operable to determine the composition of a sample site based on the spectroscopic data from plasma plume emission and the ICP-MS ion mass/charge ratio intensity data as a whole. It is found that the analysis based on LIBS optical emission spectroscopy and ICP-MS ion mass/charge ratio peak intensity data as a whole can detect far more elements, and can have greater analytical accuracy relative to LIBS emission spectroscopy or ICP-MS alone.

A multi-spectrometer system such as disclosed relative to FIGS. 8-11 can have use different types of optical spectrometers and detectors at the same time to advantage. Some embodiments comprise a scanning Czerny Turner spectrograph (CZ) coupled to an ICCD detector. This combination can effectuate extremely high sensitivity owing to maximal light throughput to the ICCD (high efficiency) from the spectrograph, and ICCD capability to amplify weak signals in the detector. Accordingly it is advantageous where the highest possible sensitivity is needed to detect numerous different elements present in the range of 1 to 10 parts per million. However this combination has the disadvantage that it can only capture a relatively narrow range of preselected wavelengths with a predetermined spectral resolution. Furthermore, the wavelength range and resolution vary inversely. The higher the spectral resolution, the narrower the range of wavelengths that can be covered at one time. Accordingly, to capture high resolution spectral information from atomic elements having spectral emissions in widely separated wavelength regions using only one CZ-ICCD, the CZ must be sequentially reconfigured to access each of the separated wavelength regions, and an additional ablation of the sample site must be performed after each reconfiguration to generate the spectral emissions for capture.

An embodiment may also include an Echelle spectrometer coupled to an ICCD detector. This combination has the advantageous capability of being able to capture a broad range of wavelengths at one time in emission from the plasma plume arising from a single ablation (a typical range is 200 nm-900 nm, although in a preferred embodiment the range is 190 nm-1040 nm and it can be greater). On the other hand, an Echelle spectrometer generally has low light throughput (low efficiency). For example an Echelle spectrometer can typically have f/10 aperture light throughput whereas a typical CZ spectrometer generally has about throughput in the range of f/3 to f/4. It can be seen that an Echelle-ICCD system is insensitive by comparison to the CZ-ICCD.

Accordingly, some embodiments comprise a plurality of CZ-ICCD spectrometers wherein each spectrometer is configured to receive a different preselected wavelength range. The plurality of spectrometers as a whole can capture a broad range of wavelengths at one time yet have very high sensitivity and resolution. The wavelength ranges can be contiguous and/or can be separated. Furthermore, various wavelength ranges can be non-overlapping or can have overlapping segments. All of the spectrometers can receive a portion of spectral emission a plasma plume simultaneously from one collection optics module through a split end fiber optic lightguide (described above with respect to FIGS. 10-11), and/or at least some of the spectrometers can receive equal portions of luminous energy from a dedicated of collection optic module as shown with respect to FIGS. 9, 11, and 12-13.

Some further embodiments comprise an array of Czerny Turner-COD optical spectrometers (e.g. each comprising a Czerny Turner monochromator with multichannel CCD detector). Each spectrometer covers a preselected, non-overlapping, wavelength region. The array of spectrometers is operable to acquire spectral data synchronously from each ablation. The embodiments have an advantage of being able to capture broadband spectral information in a wide range of wavelengths. For example, an operable range of wavelengths can be 190 nm-1040 nm, although a narrower range can be preferable for greater resolution, depending on the application. In some embodiments there can be overlapping spectrometer wavelength regions. A partially overlapping wavelength region can be useful to calibrate the response of the different spectrometers regions with respect to one another using regions of overlap.

The various detectors and monochromators/spectrographs have advantages and disadvantages with respect to one another. For example, while a CCD detector is generally less sensitivity than an ICCD, CCD technology is relatively inexpensive in comparison to an ICCD having an equivalent number of channels. A CCD detector is well suited for broadband analysis. Besides having less sensitivity, another limitation of CCD detector arrays is that they cannot be gated on and off in very short intervals to discriminate against continuum emission and/or other interference.

In the analysis of unknown samples, a broadband CCD spectrometer and/or array of spectrometers can be first used to survey the principal elements that are present, and identify the elements present in majority, minor, and/or trace concentration levels. After a sample is characterized using a broadband optical spectrometer (such as one comprising a CZ-ICCD or CZ-CCD combination), higher resolution lower intensity spectral data obtained from a high resolution, lower sensitivity spectrometer and/or plurality of high resolution/high sensitivity spectrometers in an array can be provide trace element analysis. As disclosed above, various embodiments can acquire both broadband and low intensity, high resolution spectroscopic data from a single ablation plume simultaneously.

In the foregoing specification, various aspects are described with reference to specific embodiments, but those skilled in the art will recognize that further aspects are not limited thereto. Various features and aspects described above may be used individually or jointly. Other aspects of the invention, including alternatives, modifications, permutations and equivalents of the embodiments described herein, will be apparent to those skilled in the art from consideration of the specification, study of the drawings, and practice of the various aspects. Further, various aspects can be utilized in any number of environments and applications beyond those described herein without departing from the broader spirit and scope of the description. The written description and accompanying drawings are, accordingly, to be regarded as illustrative rather than restrictive.

Although various embodiments have been presented and explained using simplified examples, it will be understood that various changes and modifications are possible with regard to materials, shapes, and dimensions, without departure from the scope of the patent claims. The embodiments and preferred features described above should be considered exemplary, with the invention being defined by the appended claims, which therefore include all such alternatives, modifications, permutations and equivalents as fall within the true spirit and scope of the present disclosure.

What is claimed is:

1. An apparatus for ablation spectroscopy, comprising:
a stage to support a sample, the stage being operable to move in x and y directions of a plane, and in a z (height) direction perpendicular to the plane during a process of laser ablation from different sites on the sample surface;
an ablation source operable to ablate material from a first sample site on the surface into a first luminous plasma plume and to ablate material from a second sample site on the surface into a second luminous plume during the process;

a position sensor operable to sense a difference in height of the first sample site relative to height of the second sample site and generate a displacement signal proportional to the difference in height, during the process;

a stage position control circuit operable to automatically maintain an optimum height of the first and the second sample sites during the process based on the displacement signal;

one or more fiber optic lightguides having at least one proximal end and a plurality of distal ends;

at least one collection optics module operable to gather light emanating from the plasma plume into the proximal end of a fiber optic lightguide;

a plurality of spectrometers, wherein each spectrometer includes wavelength separation means and a detector, and wherein each spectrometer is coupled to an associated distal end of a fiber optic lightguide; and a computer operable to receive wavelength and intensity values from each of the spectrometers, determine a representation of a sample composition based on the received wavelength and the intensity values, and output and/or record the representation and/or wavelength and intensity values;

wherein the ablation of the material from the first sample site is operable to change the height of the first sample site before the adjustment of the height of the stage and the ablation of material from the second sample site; and each of the spectrometers is operable to receive a portion of light from the plasma plume from the respectively associated distal fiber optic lightguide end, and all of the spectrometers are operable to receive the portions of the light simultaneously.

2. The apparatus of claim 1, wherein the ablation source is operable to produce a luminous plasma plume emanating light characteristic of chemical species in the sample.

3. The apparatus of claim 2, wherein the ablation source comprises a pulsable laser operable to perform the ablation and produce the luminous plasma plume.

4. The apparatus of claim 1, further comprising a triangulation laser, wherein the stage position control circuit comprises an array of motors operable to move the stage a predetermined amount.

5. The apparatus of claim 1, wherein the position sensor displacement signal depends on a laser triangulation of the first sample site and a laser triangulation of the second sample site.

6. The apparatus of claim 1, wherein the detector is operable to be insensitive to electromagnetic radiation during one time interval, and be switched on to receive the electromagnetic radiation during another different time interval.

7. The apparatus of claim 1, wherein the apparatus is operable to determine an element concentration of 20 parts per million or less in the sample.

8. The apparatus of claim 1, wherein the apparatus includes a controller operable to synchronize the positioning of the stage, the ablation of the sample, and the receiving light by each spectrometer.

9. The apparatus of claim 1, wherein the detector is operable to be insensitive to the electromagnetic radiation from the plasma plume in a time period when a ratio of continuum radiation relative to characteristic atomic line emission is relatively large, and be switched on to receive the electromagnetic radiation from the plasma plume during a different time period when the ratio of continuum radiation relative to characteristic atomic line emission is relatively small.

10. The apparatus of claim 1, further comprising an inductively coupled plasma mass spectrometer.

11. The apparatus of claim 1, wherein the apparatus is operable to perform a plurality of ablations at one selected site of the sample, and the stage position control circuit is operable to maintain one preselected pulsable laser spot size for performing each of the ablations.

12. The apparatus of claim 1, wherein the ablation source comprises a pulsable laser operable to ablate the material and produce a luminous plasma plume, the apparatus is operable to perform at least one ablation at each sample site among a plurality of different sample sites, and the stage position control system is operable to maintain one preselected laser spot size for performing each of the sample site ablations.

13. The apparatus of claim 1, wherein the apparatus is operable to set a z-value of the sample site as a parameter for ablation at the sample site, and the stage position control circuit is operable to effectuate the z-value in performing each of the ablations.

14. The apparatus of claim 1 wherein the position sensor comprises a laser displacement measuring device including a triangulation laser and a photodetector; and wherein:
the laser displacement measuring device is operable to focus a triangulation laser beam on the first sample site and sense a first reflection of the triangulation laser beam using the photodetector;

a change in the height of the second sample site is operable to produce a second reflection of the triangulation laser beam; and the displacement signal depends on a displacement between the first reflection and the second reflection.

15. The apparatus of claim 14 wherein the triangulation laser is operable to produce a visible spot on a surface of a sample site.

16. An apparatus for ablation spectroscopy, comprising:

a pulsed laser ablation source operable to ablate material from a sample site on a sample on a stage, into an emissive plasma plume with a laser pulse;

one or more collection optics modules operable to gather light emanating from the plasma plume into the proximal end of a fiber optic lightguide;

one or more fiber optic lightguides, each fiber optic lightguide having at least one proximal end operable to receive the light emanating from the plasma plume and a plurality of distal ends wherein each distal end is operable to transmit said light to an associated spectrometer for simultaneously performing trace level chemical analysis with the apparatus whereby one portion of the light can be delivered to a high sensitivity and/or low efficiency spectrometer and another portion of the light can be delivered to a low sensitivity and/or low efficiency spectrometer;

a plurality of associated spectrometers operable to acquire spectral data synchronously from each plasma plume, wherein each of the spectrometers is coupled to one associated distal end of a fiber optic lightguide and each of the spectrometers includes a wavelength separating element and a detector, and one or more of the spectrometers is collectively operable to capture broadband spectral data from each respective plasma plume;

an inductively coupled plasma mass spectrometer operable to determine ion mass to charge ratios and ion mass to charge peak intensity values arising from a gaseous portion of the ablated material;

an unreactive gas flow system operable to transport the gaseous portion of the ablated material to the inductively coupled mass spectrometer; and a computer operable to receive wavelength and wavelength intensity values from each of the optical spectrometers and to receive the ion mass to charge peak intensity values from the inductively coupled plasma mass spectrometer;

wherein:

the apparatus is operable to detect a pulse to pulse difference in the amount of material ablated from the sample site based on a signal level obtained from the broadband spectral data, and the apparatus is operable to determine a sample site composition based on a combination of the wavelength and wavelength intensity values from each of the optical spectrometers and normalized values of the ion mass to charge ratio peaks, wherein the normalization comprises a correction for the pulse to pulse differences in the amount of ablated material based on the signal level from the broadband spectral data.

17. The apparatus of claim 1 wherein the first sample site and the second sample site are the same sample site.

18. The apparatus of claim 1 wherein the first sample site and the second sample site are different sample sites.

19. An apparatus for ablation spectroscopy, comprising:

a stage to support a sample, the stage being operable to move in x and y directions of a plane, and in a z (height) direction perpendicular to the plane during a process of laser ablation from different sites on the sample surface;

an ablation source operable to ablate material from a first sample site on the surface into a first luminous plasma plume and to ablate material from a second sample site on the surface into a second luminous plume during the process;

a position sensor operable to sense a difference in height of the first sample site relative to height of the second sample site and generate a displacement signal proportional to the difference in height, during the process;

a stage position control circuit operable to automatically maintain a laser spot circle size at the first and the second sample sites during the process based on the displacement signal;

one or more fiber optic lightguides having at least one proximal end and a plurality of distal ends;

at least one collection optics module operable to gather light emanating from the plasma plume into the proximal end of a fiber optic lightguide;

a plurality of optical spectrometers, wherein each spectrometer includes wavelength separation means and a detector operable to detect spectral wavelength and wavelength intensity values, and each spectrometer is coupled to one distal end of a fiber optic lightguide;

a computer operable to receive the wavelength and intensity values from each of the spectrometers, determine a representation of a sample composition based on the received wavelength and the intensity values, and output and/or record the representation and/or wavelength and intensity values;

wherein the ablation of the material from the first sample site is operable to change the height of the first sample site before the adjustment of the height of the stage and the ablation of material from the second sample site; and each of the spectrometers is operable to receive a portion of light from the plasma plume from the respectively associated distal fiber optic lightguide end, and all of the spectrometers are operable to receive the portions of the light simultaneously.

20. The apparatus of claim 19 comprising at least one spectrometer operable to capture a relatively broadband wavelength range with relatively low resolution and low sensitivity, and at least one different spectrometer operable to simultaneously capture a relatively narrow portion of the relatively broadband wavelength range with relatively high resolution and relatively high sensitivity.

21. An apparatus for measuring composition of a sample surface, the apparatus comprising:

a pulsed laser ablation source operable to ablate material from a plurality of distinct sample sites on the sample surface into respective emissive plasma plumes;

one or more fiber optic lightguides having one proximal end and one or more distal ends;

at least one collection optics module operable to gather light emanating from each plasma plume into the proximal end of a fiber optic lightguide;

frame means for securing two different first and second collection optics modules and a laser beam focusing optics module in predetermined positions relative to one another, whereby the laser beam focusing optics module is operable to center a precise laser spot circle of predetermined size a preselected distance below the optical frame, the stage is operable to movably translate a selected sample site to the center of the laser spot circle, and each plasma plume is formed in a same relative location equidistant from the first and second collection module positions, operable for the first and second collection optics modules to capture equal portions of light from the plasma plume and optimize the light collection; and a plurality of optical spectrometers, wherein each spectrometer includes wavelength separation means and a detector operable to detect spectral wavelength and wavelength intensity values, and each spectrometer is coupled to one distal end of a fiber optic lightguide.

22. The apparatus of claim 16 comprising an array of Czerny-Turner spectrometers, wherein each of the spectrometers is configured to cover a different preselected wavelength region and the plurality of spectrometers is operable to capture a broad range of wavelengths at one time.

23. The apparatus of claim 22 wherein the broad range of wavelengths is approximately 190 nm to 1040 nm.

24. The apparatus of claim 16 comprising an Echelle spectrometer configured to capture a broad range of wavelengths at one time with relatively low sensitivity, and a Czerny-Turner spectrometer configured to capture a relatively narrow range of wavelengths at the same time with relatively high sensitivity.

25. The apparatus of claim 16 comprising: one or more spectrometers operable to capture relatively broadband spectral data from an emissive plasma plume arising from a laser pulse, wherein the apparatus is operable to detect pulse to pulse differences in the amount of material ablated based on a signal level of the broadband spectral data, and normalize and/or correct an ion mass to charge peak intensity value from the ablated material based on the detected variation.

* * * * *